United States Patent
Oh et al.

(10) Patent No.: US 11,055,843 B2
(45) Date of Patent: Jul. 6, 2021

(54) CAPSULE ENDOSCOPE FOR DETERMINING LESION AREA AND RECEIVING DEVICE

(71) Applicant: ELECTRONICS AND TELECOMMUNICATIONS RESEARCH INSTITUTE, Daejeon (KR)

(72) Inventors: Kwang Il Oh, Daejeon (KR); Tae Wook Kang, Daejeon (KR); Sung Eun Kim, Daejeon (KR); Mi Jeong Park, Daejeon (KR); Seong Mo Park, Daejeon (KR); Hyung-Il Park, Daejeon (KR); Jae-Jin Lee, Daejeon (KR); In Gi Lim, Daejeon (KR)

(73) Assignee: ELECTRONICS AND TELECOMMUNICATIONS RESEARCH INSTITUTE, Daejeon (KR)

( * ) Notice: Subject to any disclaimer, the term of this patent is extended or adjusted under 35 U.S.C. 154(b) by 530 days.

(21) Appl. No.: 16/001,750

(22) Filed: Jun. 6, 2018

(65) Prior Publication Data
US 2018/0365826 A1 Dec. 20, 2018

(30) Foreign Application Priority Data

Jun. 14, 2017 (KR) .................. 10-2017-0075090
Sep. 7, 2017 (KR) .................. 10-2017-0114741

(51) Int. Cl.
*G06T 7/00* (2017.01)
*A61B 1/00* (2006.01)
(Continued)

(52) U.S. Cl.
CPC .......... *G06T 7/0012* (2013.01); *A61B 1/0002* (2013.01); *A61B 1/00006* (2013.01);
(Continued)

(58) Field of Classification Search
CPC ......... G06T 7/0012; G06T 2207/30028; G06T 2207/30096; G06T 2207/10068; G06T 2207/20084; G06T 2207/30092; A61B 1/00032; A61B 1/00009; A61B 1/00006; A61B 1/00036; A61B 1/00016; A61B 1/041; A61B 1/0002; A61B 5/0028;
(Continued)

(56) References Cited

U.S. PATENT DOCUMENTS 8,798,049 B2 8/2014 Lim et al.
2006/0243288 A1 11/2006 Kim et al.
(Continued)

FOREIGN PATENT DOCUMENTS

JP 2009-78069 A 4/2009
KR 10-2004-0068425 A 7/2004
(Continued)

*Primary Examiner* — Peter Luong (57) ABSTRACT

Provided is a capsule endoscope. The capsule endoscope includes: an imaging device configured to perform imaging on a digestive tract in vivo to generate an image; an artificial neural network configured to determine whether there is a lesion area in the image; and a transmitter configured to transmit the image based on a determination result of the artificial neural network.

15 Claims, 12 Drawing Sheets

(51) Int. Cl.
*A61B 1/04* (2006.01)
*A61B 5/00* (2006.01)
*G16H 30/20* (2018.01)
*G06N 3/08* (2006.01)
*G16H 50/70* (2018.01)
*G16H 30/40* (2018.01)
*G06N 3/04* (2006.01)

(52) U.S. Cl.
CPC ...... *A61B 1/00009* (2013.01); *A61B 1/00016* (2013.01); *A61B 1/00032* (2013.01); *A61B 1/00036* (2013.01); *A61B 1/041* (2013.01); *A61B 5/7264* (2013.01); *G06N 3/049* (2013.01); *G06N 3/0454* (2013.01); *G06N 3/08* (2013.01); *G16H 30/20* (2018.01); *G16H 30/40* (2018.01); *G16H 50/70* (2018.01); *A61B 5/0028* (2013.01); *G06T 2207/10068* (2013.01); *G06T 2207/20084* (2013.01); *G06T 2207/30028* (2013.01); *G06T 2207/30092* (2013.01); *G06T 2207/30096* (2013.01)

(58) Field of Classification Search
CPC ........ G16H 50/70; G16H 30/40; G16H 30/20; G06N 3/0454; G06N 3/049; G06N 3/08
See application file for complete search history.

(56) References Cited

U.S. PATENT DOCUMENTS

| | | | |
|---|---|---|---|
| 2010/0274083 A1 | 10/2010 | Hyoung et al. | |
| 2012/0316421 A1* | 12/2012 | Kumar | A61B 1/041 600/407 |
| 2015/0346302 A1* | 12/2015 | Hart | A61B 5/055 702/19 |
| 2016/0342893 A1* | 11/2016 | Ross | G06N 3/063 |

FOREIGN PATENT DOCUMENTS

| | | |
|---|---|---|
| KR | 10-1063859 B1 | 9/2011 |
| WO | 2010126203 A1 | 11/2010 |

* cited by examiner

CAPSULE ENDOSCOPE FOR DETERMINING LESION AREA AND RECEIVING DEVICE

CROSS-REFERENCE TO RELATED APPLICATIONS

This U.S. non-provisional patent application claims priority under 35 U.S.C. § 119 of Korean Patent Application Nos. 10-2017-0075090, filed on Jun. 14, 2017, and 10-2017-0114741, filed on Sep. 7, 2017, the entire contents of which are hereby incorporated by reference.

BACKGROUND

The present disclosure relates to a capsule endoscope and a receiving device, and more particularly, to a capsule endoscope and a receiving device for determining a lesion area.

To examine a digestive tract in a living body, a swallowable capsule endoscope instead of a wired endoscope is being used. A capsule endoscope may identify the digestive tract without the inconvenience of a wired endoscope. The capsule endoscope may perform imaging while passing through the digestive tract such as the stomach, duodenum, small intestine, colon, and the like. The capsule endoscope may transmit images generated by imaging to a receiving device outside a body, and the receiving device may store the images.

The capsule endoscope continuously performs imaging and transmits images while passing through the digestive tract from the mouth to the anus. The capsule endoscope is usually made in pill sizes for ingestion, so a capacity and a size of a battery loaded on the capsule endoscope are limited. Therefore, a technique for reducing the power consumption of the capsule endoscope is required.

SUMMARY

The present disclosure is to provide a capsule endoscope for determining a lesion area and a receiving device.

An embodiment of the inventive concept provides a capsule endoscope including: an imaging device configured to perform imaging on a digestive tract in a living body to generate an image; an artificial neural network configured to determine whether there is a lesion area in the image; and a transmitter configured to transmit the image based on a determination result of the artificial neural network.

In an embodiment of the inventive concept, a receiving device includes: a receiver configured to receive from a capsule endoscope an image of a digestive tract in a living body and a flag bit indicating whether there is a lesion area in the image; a decoder configured to decode the flag bit and determine whether to store the image; and a storage device configured to store the image in accordance with a decoding result of the decoder.

BRIEF DESCRIPTION OF THE FIGURES

The accompanying drawings are included to provide a further understanding of the inventive concept, and are incorporated in and constitute a part of this specification. The drawings illustrate exemplary embodiments of the inventive concept and, together with the description, serve to explain principles of the inventive concept. In the drawings.

DETAILED DESCRIPTION

In the following, embodiments of the inventive concept will be described in detail so that those skilled in the art easily carry out the inventive concept.

Figure 1:
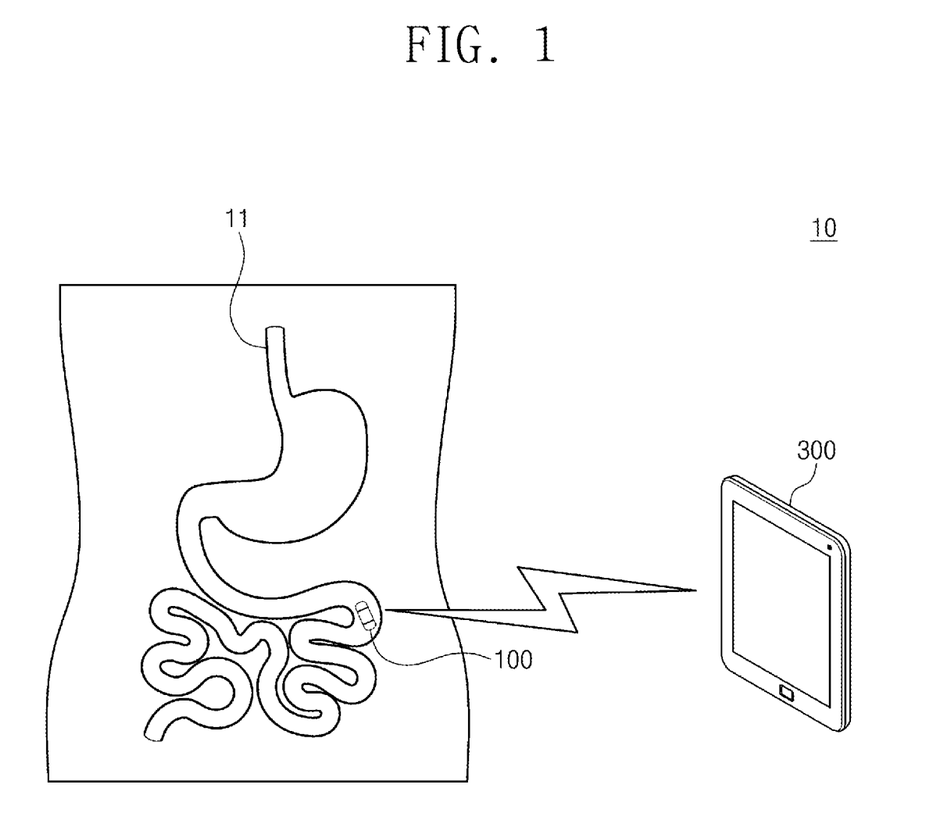
FIG. 1 is a view illustrating an exemplary capsule endoscope system according to an embodiment of the inventive concept.

FIG. 1 is a view illustrating an exemplary capsule endoscope system according to an embodiment of the inventive concept. Referring to FIG. 1, a capsule endoscope system 10 may include a capsule endoscope 100 and a receiving device 300.

The capsule endoscope 100 may pass through the digestive tract 11 in a living body. The digestive tract 11 may be referred to as a digestive organ. The living body may be referred to as a body. The capsule endoscope 100 may perform imaging on the digestive tract 11 and may produce images for the digestive tract 11. The capsule endoscope 100 may transmit the generated images to the receiving device 300 outside the living body. The transmission may be performed through wireless communication or human body communication using the human body as a medium.

According to an embodiment of the inventive concept, in order to reduce power consumption, the capsule endoscope 100 may transmit only a valid image of the generated images to the receiving device 300 instead of transmitting all the generated images to the receiving device 300. Here, the valid image represents an image having a lesion area in which the lesion of the digestive tract 11 may be suspected. Since the capsule endoscope 100 transmits only the valid image, power consumption required for transmission may be reduced.

According to another embodiment of the inventive concept, in order to reduce the amount of images generated by imaging, the capsule endoscope 100 may generate flag bits for each of the generated images. Here, the flag bits may indicate whether the images are valid images, respectively.

The receiving device 300 may store images transmitted from the capsule endoscope 100. For example, the receiving device 300 may be an electronic device such as a computer, a mobile device, a smart phone, a wearable device, a server, etc., capable of receiving, storing, or displaying an image. In an embodiment, the receiving device 300 may receive and store only the valid image from the capsule endoscope 100. In another embodiment, the receiving device 300 may store only the valid image of the received images using the flag bits described above. The receiving device 300 may filter the received images using flag bits. Thus, the power consumption required to store an image in the receiving device 300 may be reduced.

Figure 2:
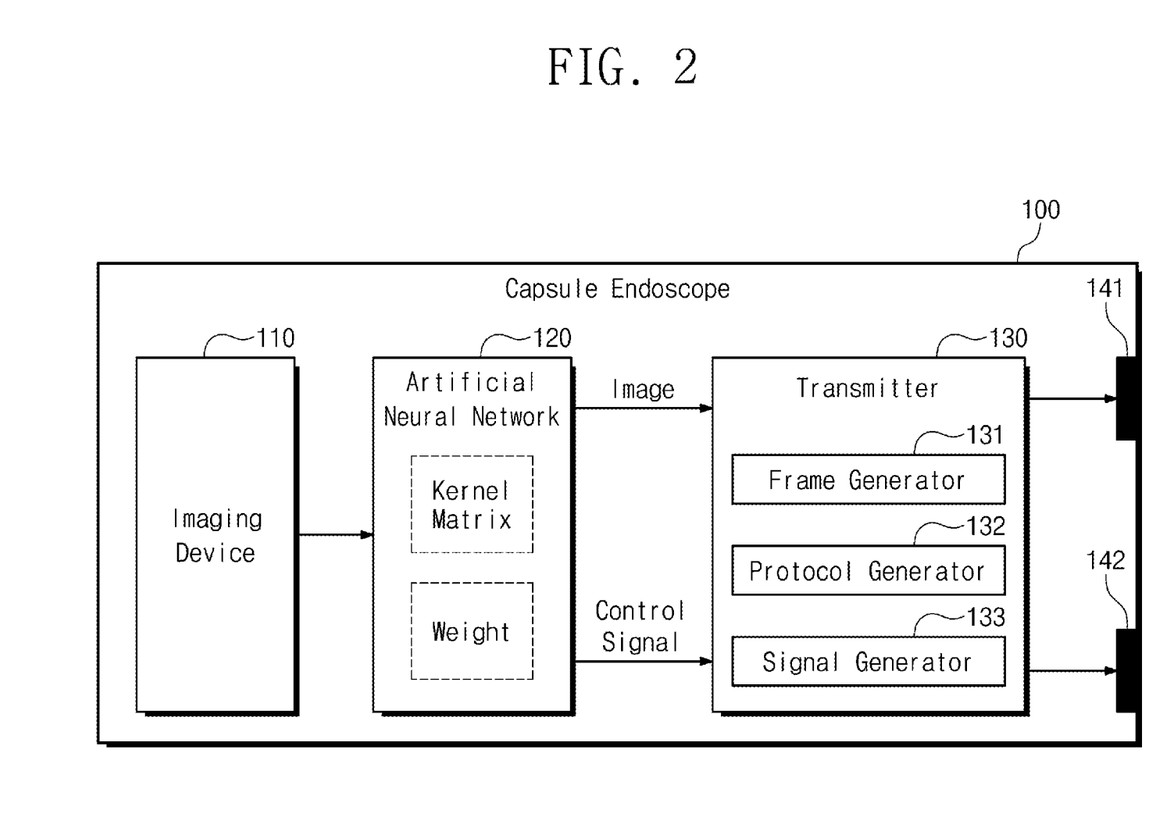
FIG. 2 is a block diagram illustrating an exemplary capsule endoscope of FIG. 1.

FIG. 2 is a block diagram illustrating an exemplary capsule endoscope of FIG. 1. Referring to FIG. 2, the capsule endoscope 100 may include an imaging device 110, an artificial neural network 120, a transmitter 130, and output ports 141 and 142.

The imaging device 110 may include, for example, an image sensor such as a charge coupled device (CCD) image sensor or a complementary metal oxide semiconductor (CMOS) image sensor. After the light is projected from the light source (not shown) in the capsule endoscope 100 to the digestive tract 11, the image sensor may sense the reflected light and generate an electrical signal. The image sensor may perform imaging on the digestive tract 11 and may produce an image (or image data). The generated image may be provided to the artificial neural network 120.

The artificial neural network 120 may determine whether there is a lesion area in the image generated by the imaging device 110. The artificial neural network 120 may be based on a deep learning engine and may more specifically be based on a convolutional neural network (CNN) used in image analysis.

The artificial neural network 120 may provide a valid image having a lesion area to the transmitter 130. Then, the artificial neural network 120 may generate a control signal for controlling the transmitter 130 based on the image determination result. The artificial neural network 120 may determine whether to activate the transmitter 130 or to supply power to the transmitter 130 using a control signal. The artificial neural network 120 may activate the transmitter 130 or may supply or provide power to the transmitter 130 when a valid image is transmitted to the transmitter 130. The artificial neural network 120 may deactivate the transmitter 130 or may not supply power to the transmitter 130 when a valid image is not transmitted to the transmitter 130. Therefore, the power consumption of the transmitter 130 may be reduced.

Referring to FIG. 2, the artificial neural network 120 may include or store a kernel matrix and a weight. Here, the kernel matrix and the weight may be used in the determination process of the artificial neural network 120, and may be data previously learned through machine learning. The kernel matrix and the weight may be updated as a result of learning whether the artificial neural network 120 has a lesion area in the image and may be included or stored back in the artificial neural network 120. A detailed image determination process by the artificial neural network 120 will be described later with reference to FIG. 3 to FIG. 7.

In an embodiment, for example, the artificial neural network 120 may be implemented in hardware within the capsule endoscope 100. The artificial neural network 120 may be implemented as a system-on-chip (SoC), an application specific integrated circuit (ASIC), or a field programmable gate array (FPGA). For example, the artificial neural network 120 may include a central processing unit (CPU), a graphical processing unit (GPU), a micro processing unit (MPU), and the like.

The transmitter 130 may transmit the image to the receiving device (see the receiving device 300 of FIG. 1) outside a living body based on the determination result of the artificial neural network 120. The transmitter 130 may operate depending on a control signal of the artificial neural network 120. The transmitter 130 may convert the digital signal constituting the image into a signal for transmission. For this, the transmitter 130 may include a frame generator 131, a protocol generator 132, and a signal generator 133.

The frame generator 131 may generate a frame of a packet for transmitting an image. More specifically, the frame generator 131 may determine where in the packet the information of the transmitter 130, the information of the receiving device, the data according to the mutually agreed protocol between the transmitter 130 and the receiving device, the image data, and the like are located in the packet.

The protocol generator 132 may generate data according to a mutually agreed protocol between the transmitter 130 and the receiving device. In an embodiment, the protocol generator 132 may generate data for performing wireless communication such as wi-fe, wigig, wibro, wimax, radio frequency identification (RFID), bluetooth, zigbee, ultra wide band (UWB), and the like. In another embodiment, the protocol generator 132 may generate data for performing human body communication with a receiving device attached to the human body.

The signal generator 133 may convert information of the transmitter 130, information of the receiving device, and data according to mutually agreed protocols between the transmitter 130 and the receiving device, and image data in the form of digital signals into analog signals. The signal generator 133 may provide analog signals to the output ports 141 and 142.

The output ports 141 and 142 may output an analog signal to the receiving device. In an embodiment, the output ports 141 and 142 may be antennas capable of transmitting analog signals according to wireless communication. In other embodiments, the output ports 141 and 142 may be electrodes capable of transmitting analog signals according to human body communication. In this case, the electric current generated depending on the potential difference between the electrodes may be transmitted to the receiving device through the human body.

Figure 3:
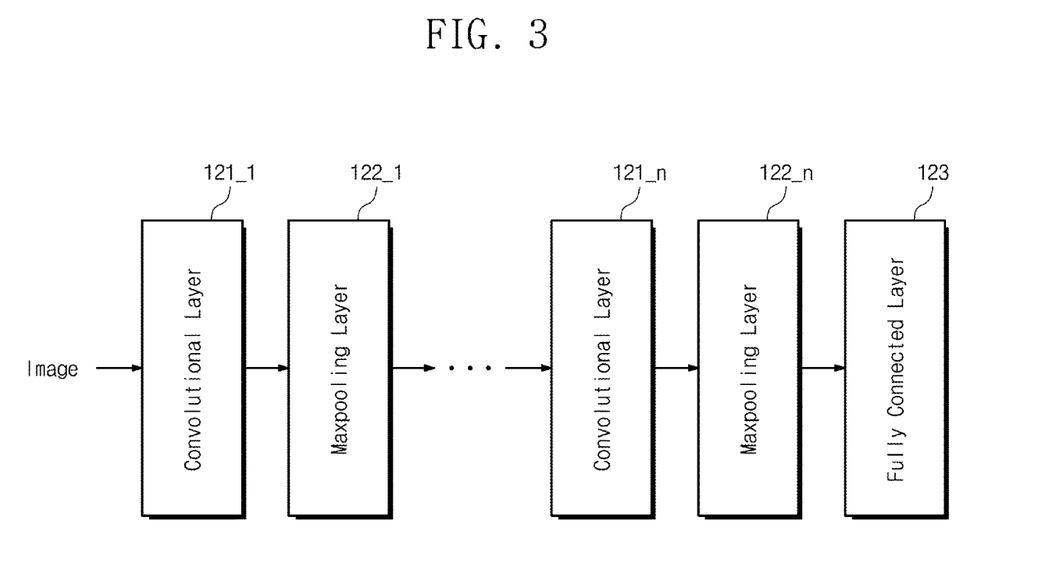
FIG. 3 is a block diagram illustrating exemplary detail layers of the artificial neural network of FIG. 2.
Figure 4:
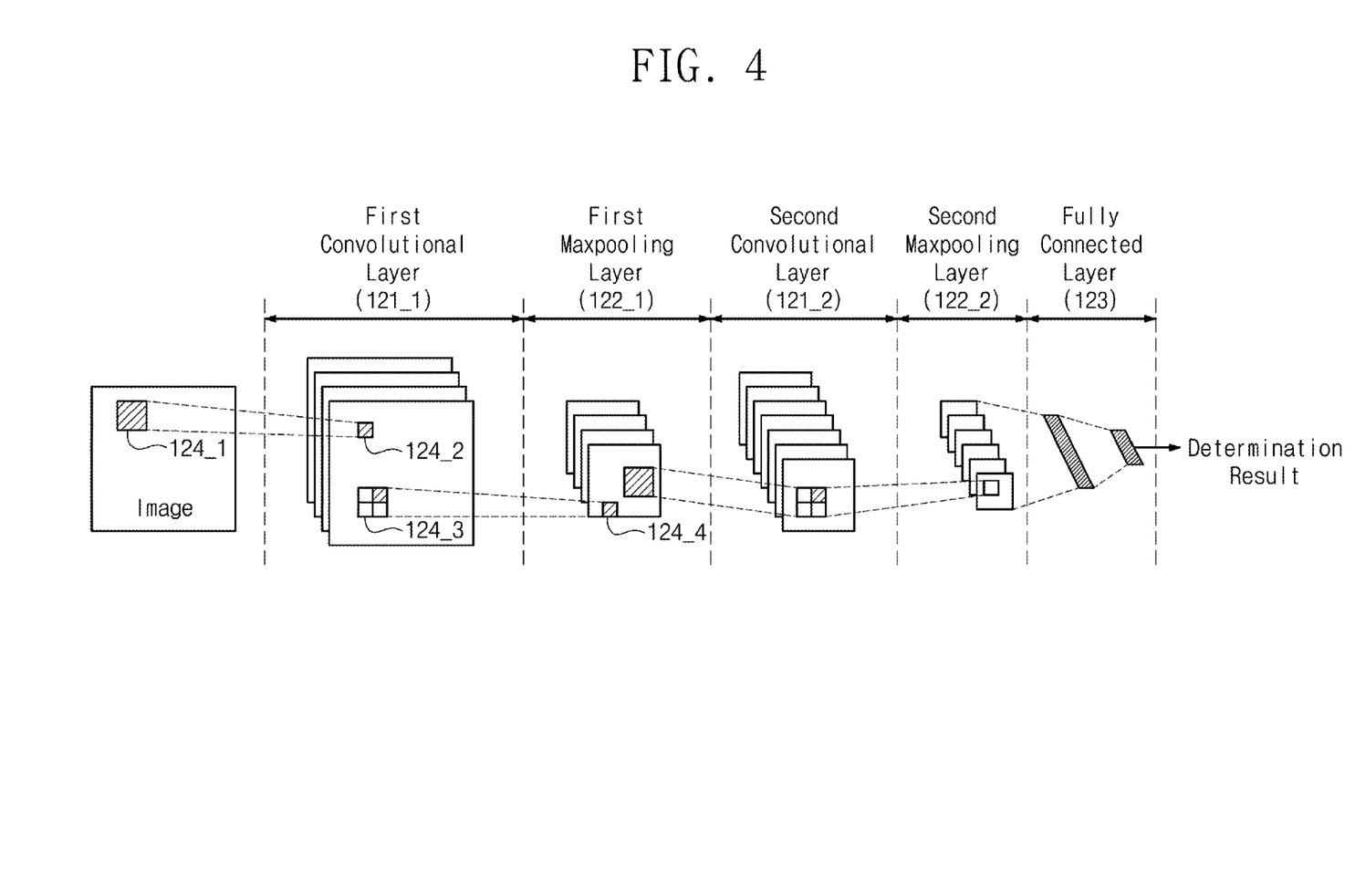
FIG. 4 is a diagram illustrating a process of analyzing an image through the detail layers of FIG. 3.

FIG. 3 is a block diagram illustrating exemplary detail layers of the artificial neural network of FIG. 2. FIG. 4 is a diagram illustrating a process of analyzing an image through the detail layers of FIG. 3. FIGS. 3 and 4 will be described together. The artificial neural network of FIGS. 3 and 4 may be based on the CNN.

Referring to FIG. 3, the artificial neural network 120 includes convolutional layers 121_1 to 121_$n$, maxpooling layers 122_1 to 122_$n$, and a fully connected layer 123. Here, n is a natural number and may be determined in advance considering the determination accuracy of the artificial neural network 120, the determination time of the artificial neural network 120, and the like. Each of the convolutional layers 121_1 to 121_$n$ and each of the maxpooling layers 122_1 to 122_$n$ may be alternately arranged.

The artificial neural network 120 may analyze the image and extract features in the image through the convolutional layers 121_1 to 121_$n$ and the maxpooling layers 122_1 to 122_$n$. The artificial neural network 120 may classify the image through the fully connected layer 123. That is, the artificial neural network 120 may determine whether there is a lesion area in the image.

Referring to FIG. 4, an exemplary process for analyzing an image when n is 2 is illustrated. In the first convolutional layer 121_1, a convolutional operation on the image and kernel matrix 124_1 may be performed. More specifically, a convolutional operation is performed on the kernel matrix 124_1 and the image area where the kernel matrix 124_1 are located in the image. The convolutional result 124_2 may indicate how similar the image area is to the kernel matrix 124_1. For example, as the convolutional result 124_2 is greater, the degree of similarity between the image area and the kernel matrix 124_1 becomes greater. The kernel matrix 124_1 may be moved by stride in the image and the convolutional operation may be iteratively performed so that the entire image may be scanned or filtered. Convolutional results may be gathered and new images may be generated. Here, the number of new images may be determined according to the number of kernel matrices, and the size of the new images may be determined by the size of the image generated by the imaging device 110 (see FIG. 2), the size of the kernel matrix, strides, padding, and the like.

In the first maxpooling layer 122_1, sampling on the new images may be performed. The pixel 124_4 having the maximum value of the pixels in the sampling filter 124_3 may be sampled. Similar to the convolutional operation, the sampling filter 124_3 may be moved by stride in the image containing the convolutional results, and the sampling may be performed iteratively. Pixels having the maximum value may be gathered and new images may be generated. Here, as the sampling is performed, the size of the image may be reduced. Operations in the second convolutional layer 121_2 and the second maxpooling layer 122_2 are substantially similar to operations in the first convolutional layer 121_1 and the first maxpooling layer 122_1. That is, the image may pass through at least one convolutional layer and at least one maxpooling layer, and features of the image may be extracted in the pass-through process.

In the fully connected layer 123, the results of passing through the first convolutional layer 121_1, the first maxpooling layer 122_1, the second convolutional layer 121_2, and the second maxpooling layer 122_2 may be classified. The fully connected layer 123 may include artificial neurons, and the artificial neurons may be connected through a synapse. Herein, the intensity of the synapse or the degree of coupling of artificial neurons may be determined by the weights included or stored in the artificial neural network 120. The artificial neural network 120 may determine whether the image includes lesions such as bleeding, polyps, and the like.

Figure 5:
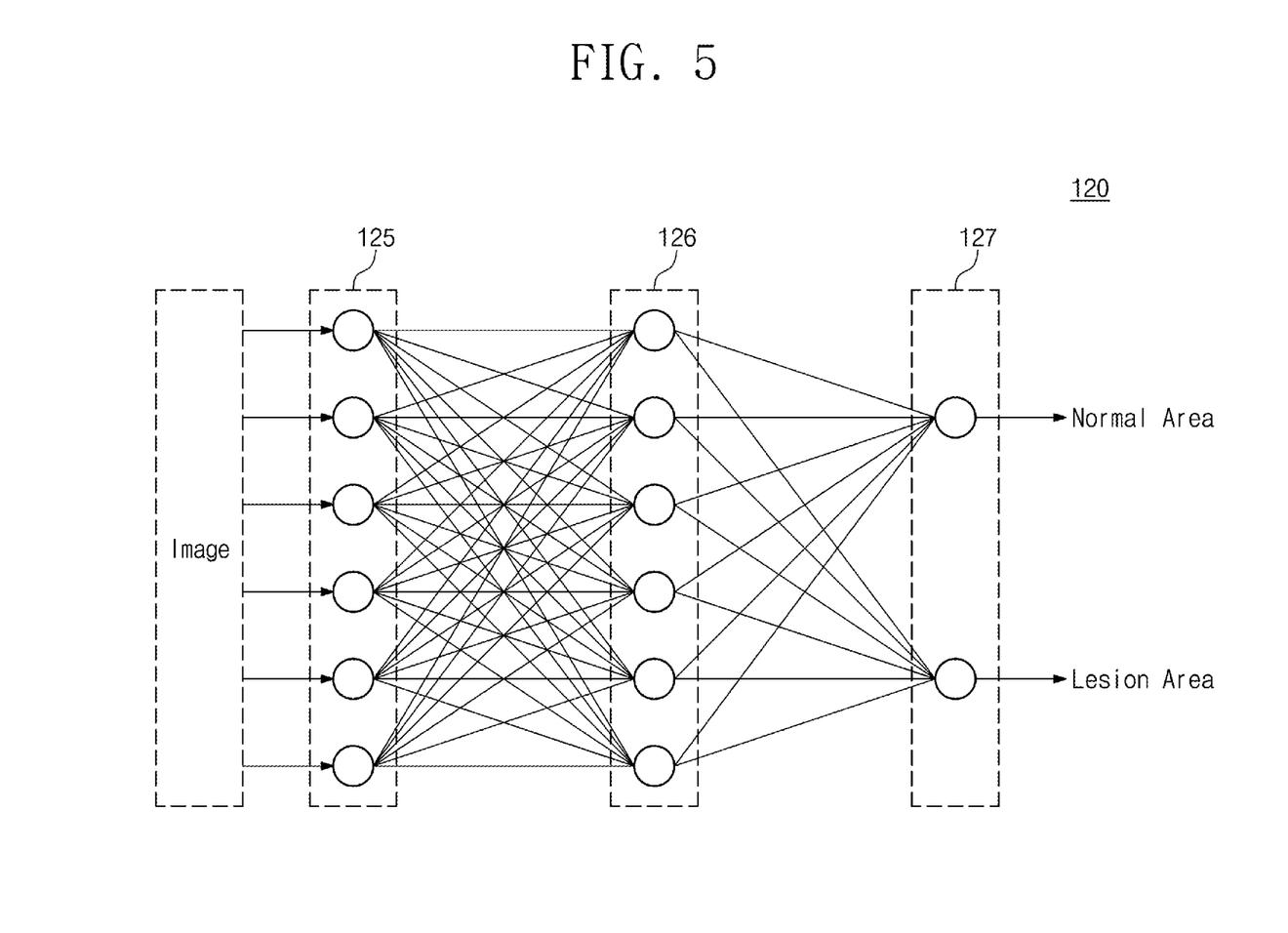
FIG. 5 is a block diagram illustrating exemplary detail layers of the artificial neural network of FIG. 2.
Figure 6:
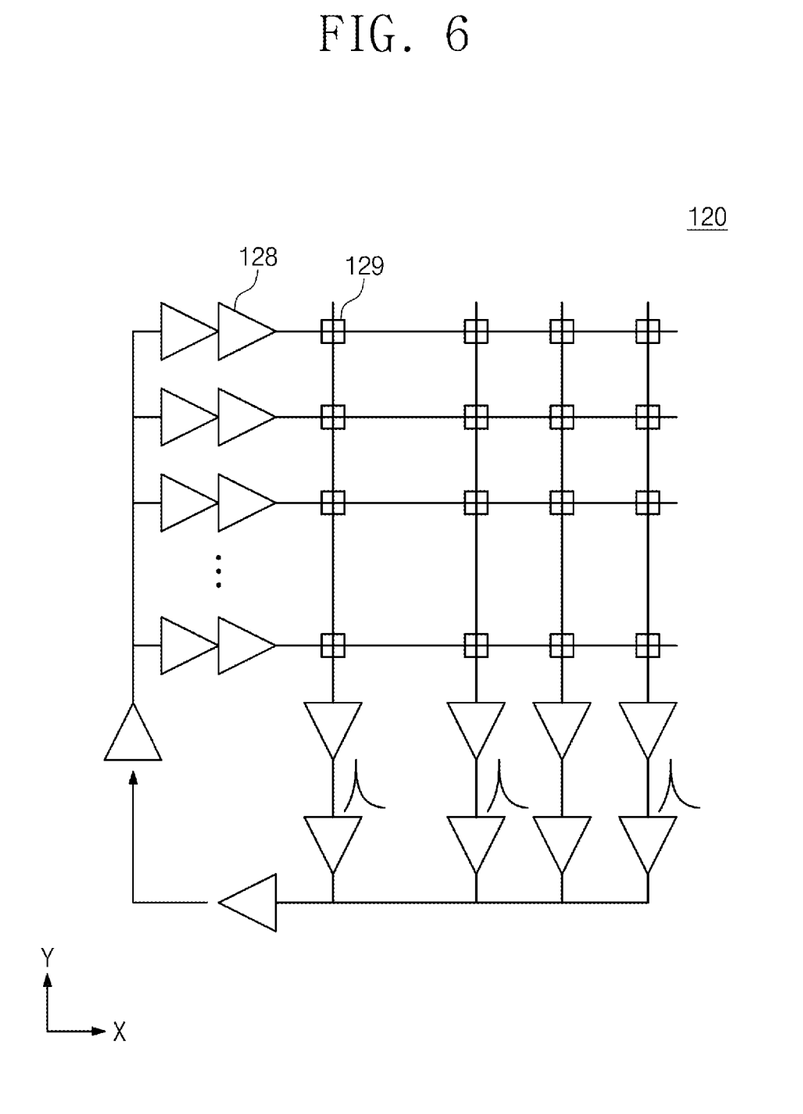
FIG. 6 is a diagram illustrating an example in which the detail layers of FIG. 5 are implemented.

FIG. 5 is a block diagram illustrating exemplary detail layers of the artificial neural network of FIG. 2. FIG. 6 is a diagram illustrating an example in which the detail layers of FIG. 5 are implemented. FIGS. 5 and 6 will be described together. The artificial neural network 120 of FIGS. 5 and 6 may be based on spiking neural network (SNN). The SNN may use independent spikes and may be simply implemented than the CNN. In comparison with the CNN, since the SNN may have a simple structure, power consumption and of SNN may be lower than power consumption of CNN and an area of SNN may be smaller than an area of the CNN.

Referring to FIG. 5, the artificial neural network 120 may include an input layer 125, a hidden layer 126, and an output layer 127. The input layer 125 may receive image generated by the imaging device 110. Each of artificial neurons of the input layer 125 may output spikes to artificial neurons of the hidden layer 126 based on the image. Each of the artificial neurons of the hidden layer 126 may determine whether to output spikes to the output layer 127, based on the spikes received from the input layer 125. For example, each of the artificial neurons of the hidden layer 126 may accumulate the spikes received from the input layer 125 and may output spikes to the output layer 127 when the accumulation result reaches a threshold value.

For brevity of illustration, it is illustrated that the number of hidden layer 126 is one in FIG. 5, but the number of hidden layer 126 may be one or more. In this case, each of the artificial neurons of the hidden layer 126 may output spikes to another hidden layer (not shown) based on the spikes received from the input layer 125. Further, the number of artificial neurons included in each of the layers 125, 126, and 127 is only exemplary.

The output layer 127 may output whether there is a lesion area in the image generated by the imaging device 110. For example, the output layer 127 may output that the image input to the input layer 125 corresponds to a normal area. The output layer 127 may output that the image input to the input layer 125 corresponds to a lesion area. For example, an accuracy of determination results (outputs of the output layer 127) based on the SNN may be lower than an accuracy of determination results (outputs of the fully connected layer 123) based on the CNN. If there is a lesion area in the image, the CNN may perform a diagnosis on the lesion area. That is, the CNN may determine diagnostic information related to the lesion area. However, the SNN may only determine whether the image corresponds to a normal area or a lesion area. Further, the SNN may determine whether there is a suspect lesion area in the image. Although an accuracy of determination of the SNN may be lower than the CNN, the capsule endoscope 100 may only transmit an image having a lesion area or an image having a suspect lesion area by using the artificial neural network 120 based on the SNN.

In FIG. 6, an example in which the artificial neural network 120 based on the SNN is implemented in hardware manner is illustrated. For example, artificial neurons 128 of the layers 125, 126, and 127 may be arranged along the X-axis or Y-axis. Each of synapses 129 located at the interconnections of the X-axis and Y axis may indicate the degree of coupling of the artificial neurons 128. The synapses 129 may be determined by weights included or stored in the artificial neural network 120. The number of synapses 129 in FIG. 6 is not limited thereto.

Figure 7:
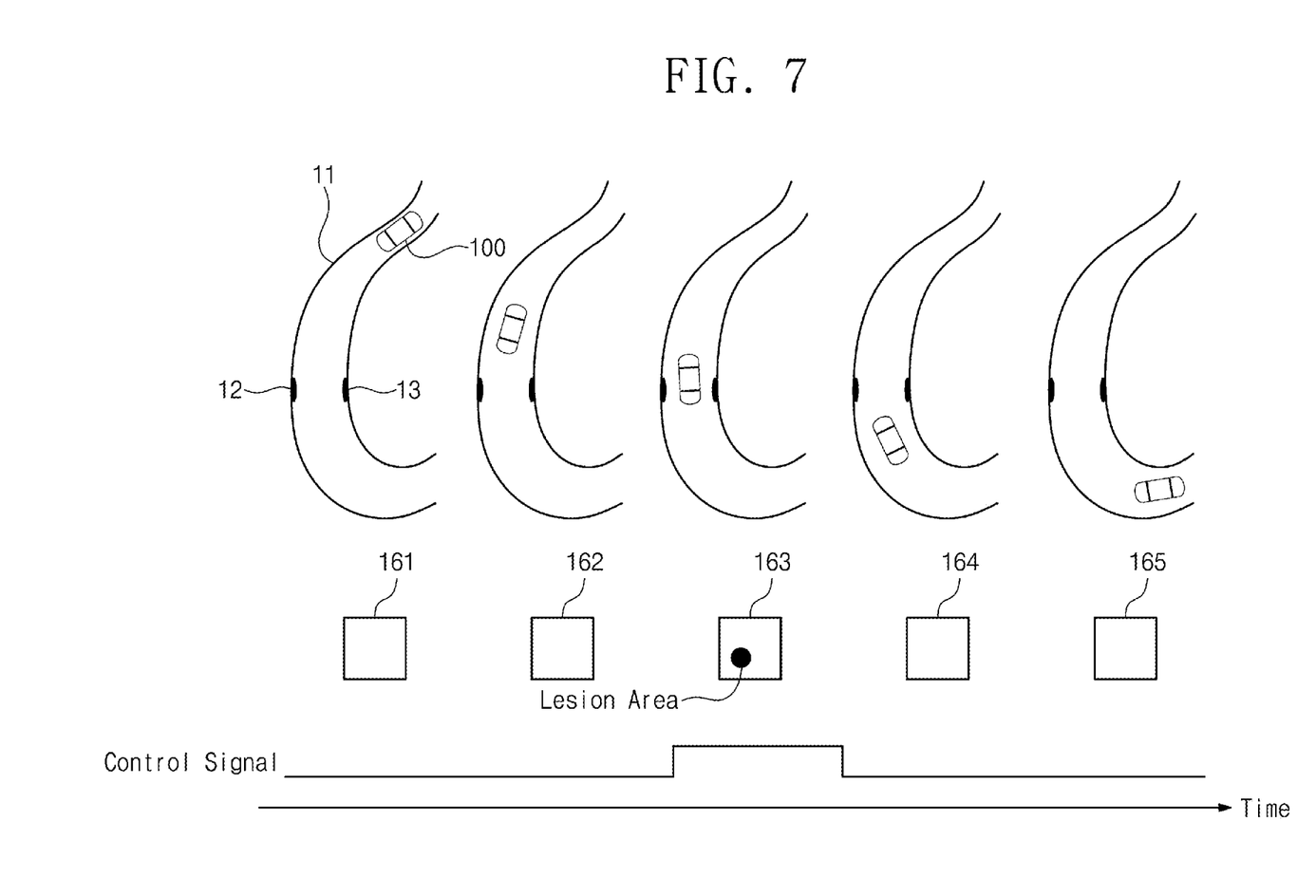
FIG. 7 is a view showing a process of passing the capsule endoscope of FIG. 2 through a digestive tract.

FIG. 7 is a view showing a process of passing the capsule endoscope of FIG. 2 through a digestive tract. In FIG. 7, the horizontal axis represents a time, and it is assumed that the lesions 12 and 13 are present in the digestive tract 11.

The capsule endoscope 100 may generate images 161 to 165 while passing through the digestive tract 11. The artificial neural network 120 may determine a valid image 163 having a lesion area of the images 161 to 165. Then, the artificial neural network 120 may generate a control signal to control the transmitter 130. For example, the artificial neural network 120 may set the control signal to logic 0 during intervals corresponding to images 161, 162, 164, and 165, and may set the control signal to logic 1 during the interval corresponding to the valid image 163. Here, the logic states of the control signal may be set as opposed to those shown in the drawing. The transmitter 130 may operate only in the interval corresponding to the valid image 163 depending on the control signal.

Figure 8:
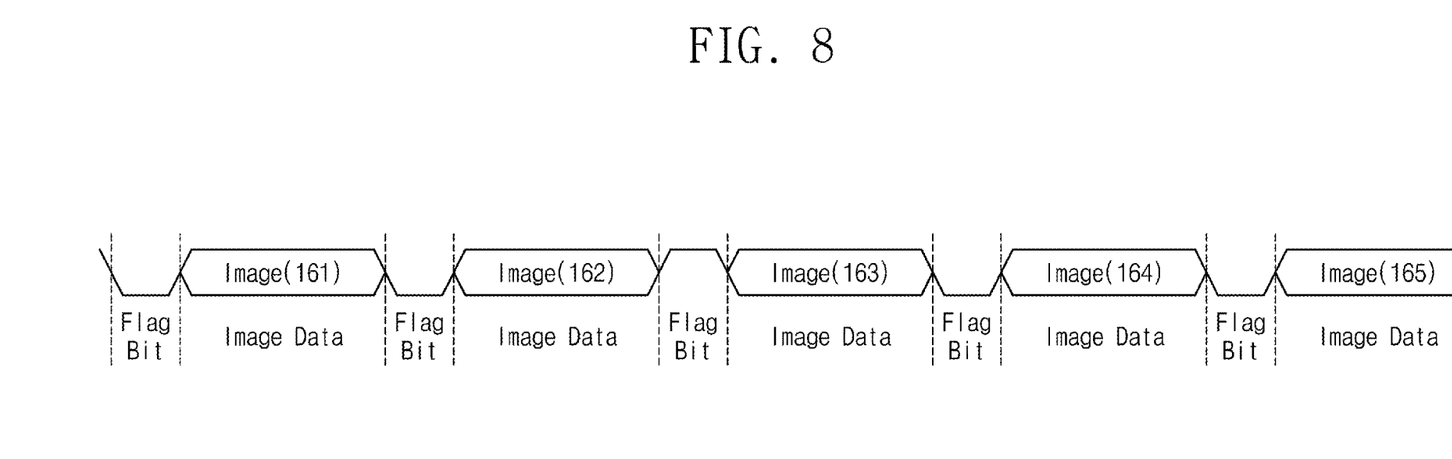
FIG. 8 is a diagram illustrating an exemplary packet transmitted by the capsule endoscope of FIG. 2.

FIG. 8 is a diagram illustrating an exemplary packet transmitted by the capsule endoscope of FIG. 2. FIG. 8 relates to the case where the capsule endoscope 100 transmits the images 161 to 165 as well as the valid image 163 to a receiving device.

The artificial neural network 120 may determine whether there is a lesion area in each of the images 161 to 165. The artificial neural network 120 may provide the transmitter 130 with the determination results for the images 161 to 165 and the images 161 to 165, respectively. The transmitter 130 may generate flag bits, each representing the determination results of the artificial neural network 120, and may transmit the flag bits with the images 161 to 165 to the receiving device. For example, the value of the flag bit may be logic 1 if the corresponding image is a valid image and may be logic 0 if the image is not a valid image.

In an embodiment, the frame generator 131 of the transmitter 130 may determine the location of the flag bits and the location of the image data. Referring to FIG. 8, the frame generator 131 may determine the location of a flag bit such that a flag bit may be transmitted to the receiving device before the image data.

Figure 9:
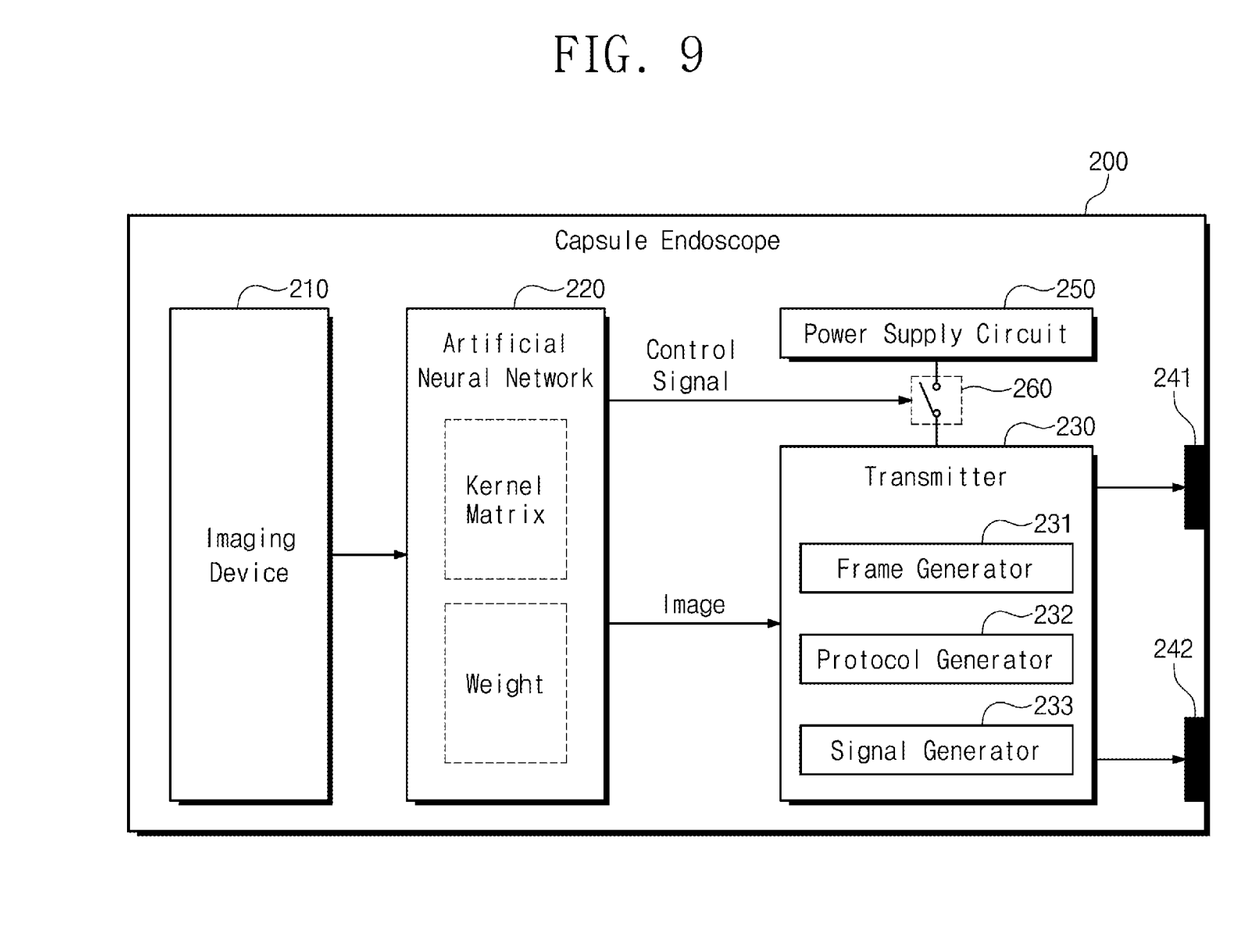
FIG. 9 is a block diagram illustrating an exemplary capsule endoscope according to another embodiment of the inventive concept.

FIG. 9 is a block diagram illustrating an exemplary capsule endoscope according to another embodiment of the inventive concept. Referring to FIG. 9, the capsule endoscope 200 may include an imaging device 210, an artificial neural network 220, a transmitter 230, output ports 241 and 242, a power supply circuit 250, and a switch 260. Here, the imaging device 210, the artificial neural network 220, the transmitter 230, and the output ports 241 and 242 perform the same functions as the imaging device 110, the artificial neural network 120, the transmitter 130, and the output ports 141 and 142 of the FIG. 2, respectively. The difference between the capsule endoscope 200 and the capsule endoscope 100 will be described below.

The power supply circuit 250 may supply power to the components of the capsule endoscope 200. For example, the power supply circuit 250 may be a battery. Referring to FIG. 9, although the power supply circuit 250 is illustrated as supplying power only to the transmitter 230 through the switch 260, the power supply circuit 250 may also supply power to the imaging device 210 and the artificial neural network 220.

The switch 260 may be turned on or turned off depending on the control signal of the artificial neural network 220. For example, if the artificial neural network 220 determines that there is a lesion area in the image of the imaging device 210 and activates the control signal, the switch 260 may be turned on, and if not, may be turned off. When the switch 260 is turned off, since the transmitter 230 does not transmit an image other than a valid image, the power consumption of the capsule endoscope 200 may be reduced.

Figure 10:
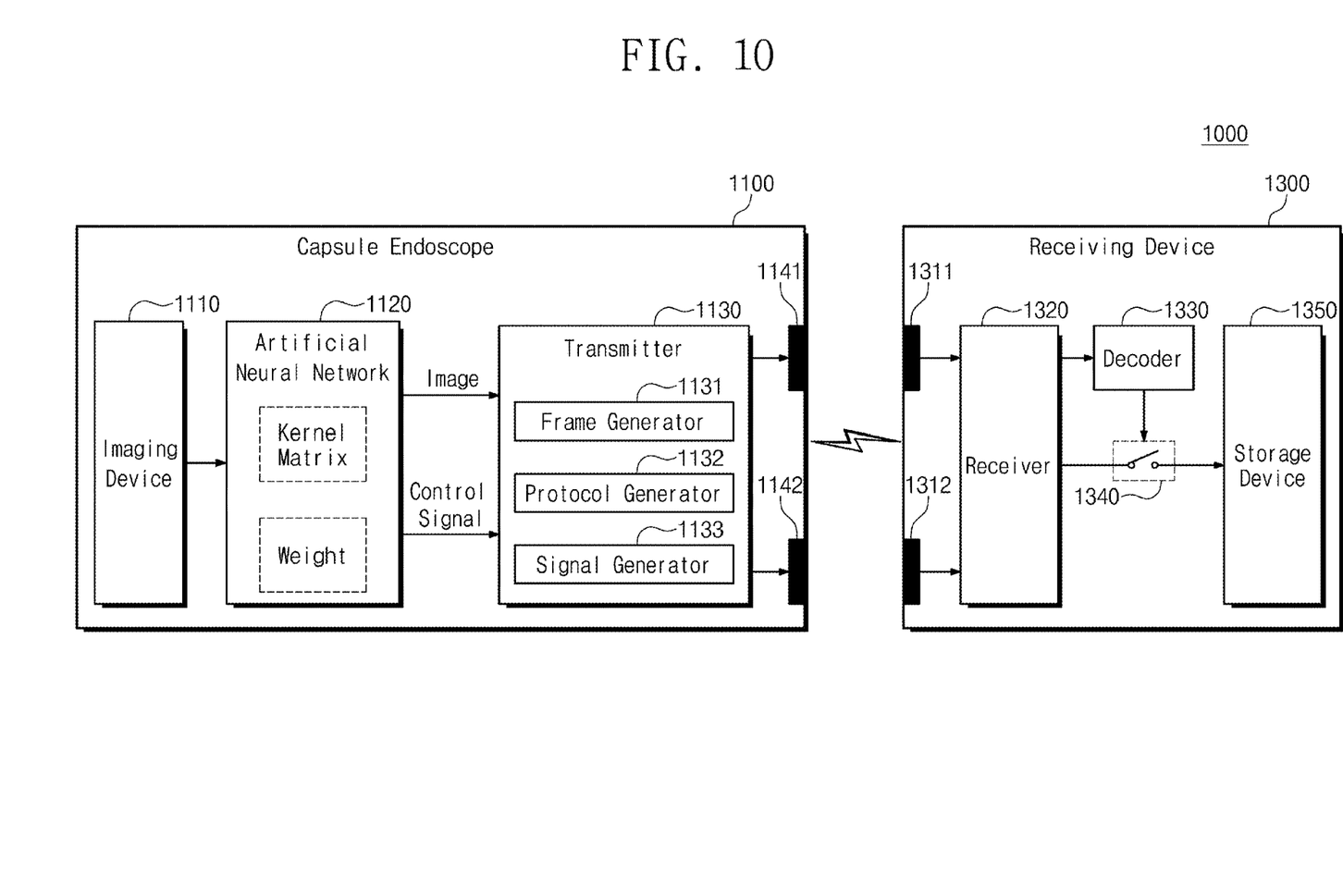
FIG. 10 is a block diagram illustrating a capsule endoscope, a receiving device, and a capsule endoscope system according to an embodiment of the inventive concept.

FIG. 10 is a block diagram illustrating a capsule endoscope, a receiving device, and a capsule endoscope system according to an embodiment of the inventive concept. A capsule endoscope system 1000 may include a capsule endoscope 1100 and a receiving device 1300. The capsule endoscope 1100 may be the capsule endoscope 100 of FIG. 2 or the capsule endoscope 200 of FIG. 9. Here, the imaging device 1110, the artificial neural network 1120, the transmitter 1130, and the output ports 1141 and 1142 perform the substantially same functions as the imaging device 110, the artificial neural network 120, the transmitter 130, and the output ports 141 and 142, respectively. The receiving device 1300 may include input ports 1311 and 1312, a receiver 1320, a decoder 1330, a switch 1340, and a storage device 1350.

In an embodiment, the input ports 1311 and 1312 may be antennas capable of receiving analog signals according to wireless communication. In other embodiments, the input ports 1311 and 1312 may be electrodes capable of receiving analog signals according to human body communication. In this case, the input ports 1311 and 1312 may be attached to the human body.

The receiver 1320 may receive an image in the form of an analog signal from the capsule endoscope 1100 through the input ports 1311 and 1312. The receiver 1320 may convert the analog signal to a digital signal according to a protocol previously agreed with the transmitter of the capsule endoscope 1100. During the conversion process, the receiver 1320 may amplify and filter the analog signal. The receiver 1320 may provide the storage device 1350 with an image transmitted by the capsule endoscope 1100.

In an embodiment, the capsule endoscope 1100 may transmit a valid image having a lesion area to the receiving device 1300. In this case, the valid image may be stored in the storage device 1350 as it is, and the receiving device 1300 may not include the decoder 1330 and the switch 1340 as shown in the drawing.

In another embodiment, the capsule endoscope 1100 may transmit to the receiving device 1300 images and flag bits indicating whether each of the images is a valid image, like a packet of FIG. 8. In this case, the decoder 1330 may decode the flag bits and determine whether to store the images. The decoder 1330 may control the switch 1340 based on the decoding result.

If the flag bit indicates that the image is a valid image, the switch 1340 may be turned on, or if not, may be turned off. Accordingly, only the valid image of the received images may be provided to the storage device 1350, and other images other than the valid image may not be provided.

The storage device 1350 may store the image depending on the decoding result of the decoder 1330. A valid image having a lesion area of the images received from the capsule endoscope 1100 may be stored in the storage device 1350 and other images other than the valid image may not be stored in the storage device 1350. If the receiver 1320 receives only the valid image from the capsule endoscope 1100, the storage device 1350 may store the valid image received by the receiver 1320 as it is.

The storage device 1350 may be any of a variety of storage devices including, for example, a dynamic random access memory (DRAM), a static random access memory (SRAM), a read only memory (ROM), a programmable ROM (PROM), an electrically programmable ROM (EPROM), an electrically erasable and programmable ROM (EEPROM), a solid state drive (SSD), a hard disk drive (HDD), a NAND flash memory, a NOR flash memory, a magnetic random access memory (MRAM), a phase-change random access memory (PRAM), a ferroelectric random access memory (FRAM), a thyristor random access memory (TRAM), and the like.

Figure 11:
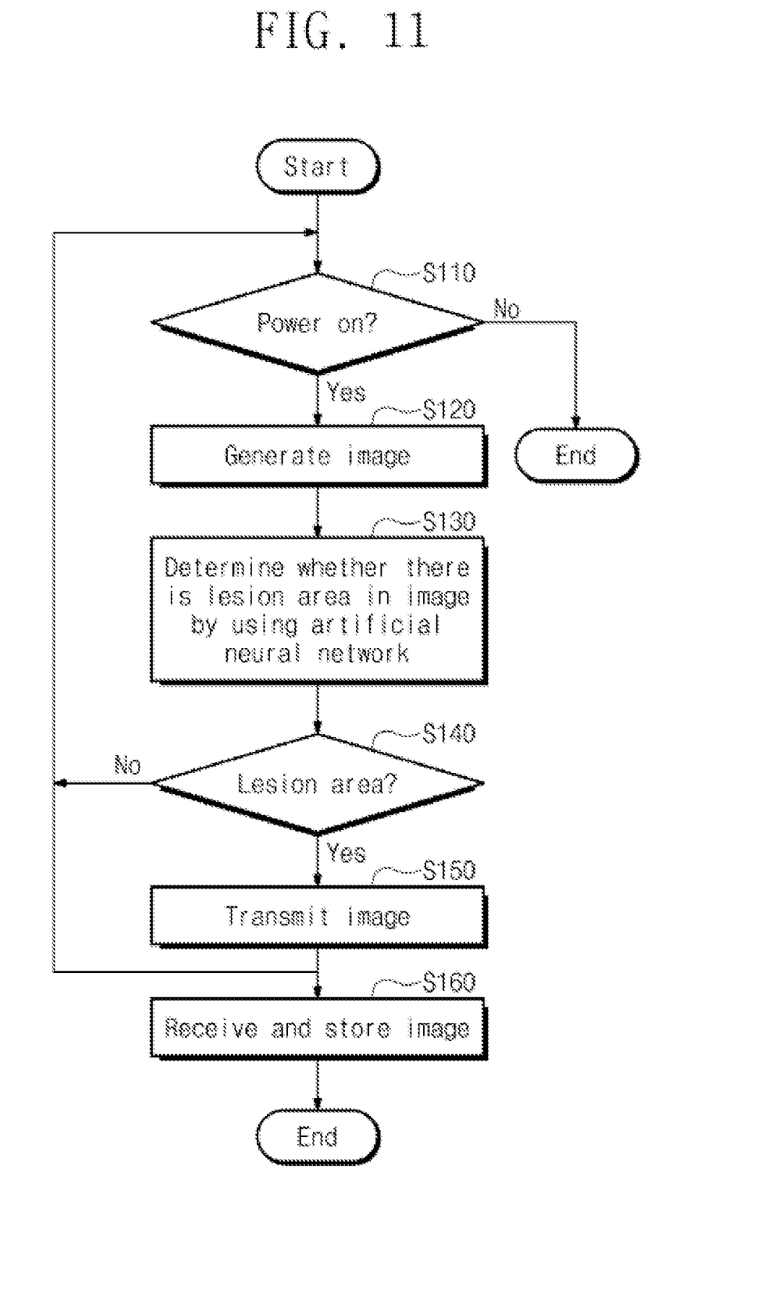
FIG. 11 is a flowchart illustrating exemplary operations of the capsule endoscope and the receiving device of FIG. 10.

FIG. 11 is a flowchart illustrating exemplary operations of the capsule endoscope and the receiving device of FIG. 10. Referring to FIG. 11, operations S110 to S150 are the operations of the capsule endoscope 1100, and operation S160 is the operation of the receiving device 1300.

In operation S110, it may be determined whether the capsule endoscope 1100 is powered on or whether the battery is capable of supplying power. If the power is on (Yes), operation S120 proceeds, and if the power is off (No), the capsule endoscope 1100 no longer operates.

In operation S120, the capsule endoscope 1100 may perform imaging on the digestive tract and may generate an image. The period and interval of the imaging of the capsule endoscope 1100 may be predetermined. In an embodiment, the period and interval of the imaging may vary depending on the speed of movement of the capsule endoscope 1100. In another embodiment, in order for the capsule endoscope to produce an image for a particular digestive tract, performing the imaging may be determined depending on the position of the capsule endoscope 1100 or the elapsed time after the capsule endoscope 1100 is inserted into the human body.

In operation S130, the capsule endoscope 1100 may determine whether there is a lesion area in the image generated in operation S120. For this purpose, the capsule endoscope 1100 may include an artificial neural network 1120 based on CNN or an artificial neural network 1120 based on SNN. In the artificial neural network 1120, a previously learned kernel matrix and weight may be stored to determine an image.

In operation S140, if there is a lesion area in the image generated in operation S120 (Yes), operation S150 is performed. If there is no lesion area in the image (No), operation S110 is performed.

In operation S150, the capsule endoscope 1100 may transmit a valid image having a lesion area of the images regularly or irregularly generated in operation S120 to the receiving device 1300. Then, the capsule endoscope 1100 may perform operation S110 again. In operations other than operation S150, the transmitter transmitting the image may be deactivated or power may not be supplied to the transmitter.

In operation S160, the receiving device 1300 may receive and store the image. The image received in operation S160 is a valid image. Since only the valid image is stored in the receiving device 1300, the storage capacity of the receiving device 1300 may decrease. Also, the amount of image that a user (e.g., a doctor) has to determine may be reduced and the determination time may be reduced.

Figure 12:
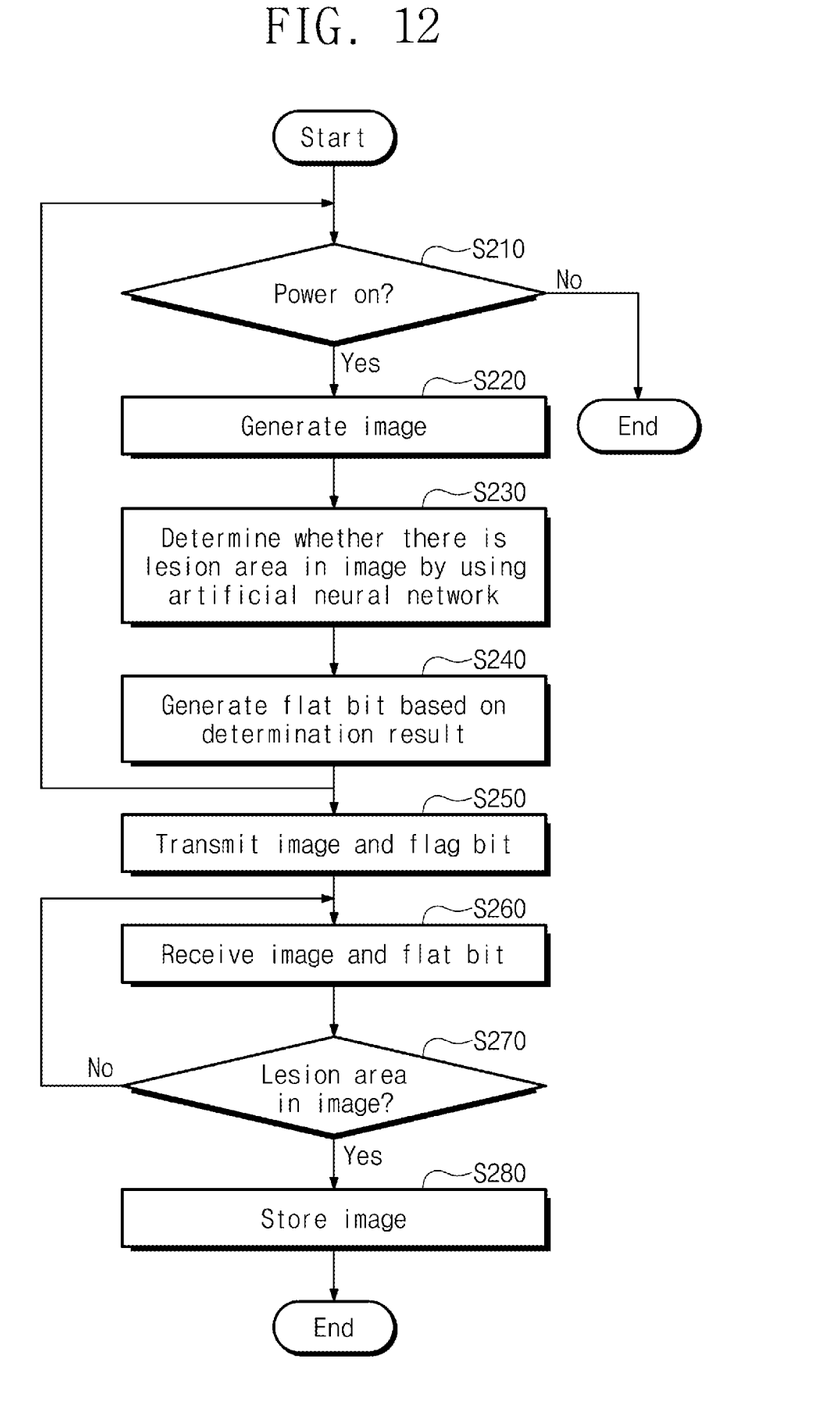
FIG. 12 is a flowchart illustrating exemplary operations of the capsule endoscope and the receiving device of FIG. 10.

FIG. 12 is a flowchart illustrating exemplary operations of the capsule endoscope and the receiving device of FIG. 10. Referring to FIG. 12, operations S210 to S250 are operations of the capsule endoscope 1100, and operations S260 to S280 are operations of the receiving device 1300. In FIG. 12, operation S210, operation S220, and operation S230 are substantially the same as operation S110, operation S120, and operation S130 in FIG. 11, respectively.

In operation S240, the capsule endoscope 1100 may generate a flag bit based on the determination result of operation S230. The flag bit may indicate the determination result of operation S230. That is, the flag bit may indicate whether the image generated in operation S220 is a valid image.

In operation S250, the capsule endoscope 1100 may transmit the image generated in operation S220 and the flag bit generated in operation S240 to the receiving device 1300. Then, the capsule endoscope 1100 may perform operation S210 repeatedly.

In operation S260, the receiving device 1300 may receive the image and the flag bit. In operation S270, the receiving device 1300 may determine through the flag bit whether the image has the lesion area. If the image has a lesion area (Yes), the image may be stored in operation S280. If the image does not have the lesion area (No), operation S260 may be performed again.

The capsule endoscope according to the embodiment of the inventive concept may reduce power consumption by transmitting only an image having a lesion area.

A receiving device according to an embodiment of the inventive concept may store only an image having a lesion area using a flag bit. Thus, the amount of image stored in the receiving device may be reduced. Further, since the amount of the image to be determined in determining the image is reduced, the determining time may be reduced.

Although the exemplary embodiments of the inventive concept have been described, it is understood that the inventive concept should not be limited to these exemplary embodiments but various changes and modifications can be made by one ordinary skilled in the art within the spirit and scope of the inventive concept as hereinafter claimed.

What is claimed is:

1. A capsule endoscope comprising:
    an imaging device configured to perform imaging on a digestive tract in a living body to generate an image;
    an artificial neural network configured to determine whether there is a lesion area in the image; and
    a transmitter configured to transmit the image based on a determination result of the artificial neural network,
    wherein the transmitter generates a flag bit indicating the determination result of the artificial neural network, and transmits the flag bit together with the image.

2. The capsule endoscope of claim 1, wherein the artificial neural network is based on convolution neural network (CNN).

3. The capsule endoscope of claim 2, wherein the artificial neural network stores a kernel matrix for determining pixels in the image and a weight indicating a degree of coupling of neurons in the CNN.

4. The capsule endoscope of claim 3, wherein the kernel matrix and the weight are previously learned data.

5. The capsule endoscope of claim 4, wherein the kernel matrix and the weight are updated by the artificial neural network.

6. The capsule endoscope of claim 1, wherein the artificial neural network activates the transmitter if the lesion area is present in the image and generates a control signal for deactivating the transmitter if the lesion area is not present in the image.

7. The capsule endoscope of claim 6, further comprising:
    a power supply circuit configured to supply power to the imaging device, the artificial neural network, and the transmitter; and
    a switch configured to connect the power supply circuit and the transmitter.

8. The capsule endoscope of claim 7, wherein the switch connects the power supply circuit and the transmitter in accordance with the control signal.

9. The capsule endoscope of claim 1, wherein the artificial neural network is based on spiking neural network (SNN).

10. The capsule endoscope of claim 9, wherein the artificial neural network a weight indicating a degree of coupling of neurons in the SNN.

11. A receiving device comprising:
    a receiver configured to receive from a capsule endoscope an image of a digestive tract in a living body and a flag bit indicating whether there is a lesion area in the image;
    a decoder configured to decode the flag bit and determine whether to store the image; and
    a storage device configured to store the image in accordance with a decoding result of the decoder.

12. The receiving device of claim 11, wherein the decoder decodes the flag bit before the image is stored in the storage device to determine whether the lesion area is present in the image.

13. The receiving device of claim 12, wherein if the lesion area is present in the image, the image is stored in the storage device, and if the lesion area is not present in the image, the image is not stored in the storage device.

14. The receiving device of claim 11, wherein the flag bit indicates a result that the artificial neural network of the capsule endoscope determines whether the lesion area is present in the image.

15. A capsule endoscope comprising:
- an imaging device configured to perform imaging on a digestive tract in a living body to generate an image;
- an artificial neural network configured to determine whether there is a lesion area in the image; and
- a transmitter configured to transmit the image based on a determination result of the artificial neural network,
- wherein the artificial neural network activates the transmitter if the lesion area is present in the image and generates a control signal for deactivating the transmitter if the lesion area is not present in the image.

* * * * *